US011260019B2

(12) United States Patent
Hajduk et al.

(10) Patent No.: US 11,260,019 B2
(45) Date of Patent: Mar. 1, 2022

(54) ANHYDROUS COSMETIC COMPOSITIONS COMPRISING PEARLESCENT PIGMENT AND A DIESTER

(71) Applicant: L'OREAL, Paris (FR)

(72) Inventors: Monika Hajduk, Westfield, NJ (US); Shirley Carter, Middlesex, NJ (US); Oscar Mata, Dunellen, NJ (US); Diana Fernandez, Elizabeth, NJ (US); Lisa Voorhees, Middlesex, NJ (US); Erika Menoni, Fanwood, NJ (US); Cristina Dubceac, Fremont, CA (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/586,390

(22) Filed: Sep. 27, 2019

(65) Prior Publication Data

US 2021/0093548 A1  Apr. 1, 2021

(51) Int. Cl.
*A61K 8/02* (2006.01)
*A61K 8/96* (2006.01)
*A61Q 1/02* (2006.01)
*A61K 8/25* (2006.01)
*A61K 8/37* (2006.01)
*A61K 8/92* (2006.01)

(52) U.S. Cl.
CPC .............. *A61K 8/965* (2013.01); *A61K 8/022* (2013.01); *A61K 8/25* (2013.01); *A61K 8/37* (2013.01); *A61K 8/92* (2013.01); *A61Q 1/02* (2013.01)

(58) Field of Classification Search
None
See application file for complete search history.

(56) References Cited

U.S. PATENT DOCUMENTS

| 4,534,963 A | 8/1985 | Gordon |
| 9,895,295 B2 * | 2/2018 | Mac Dermott ......... A61K 8/361 |
| 2018/0185250 A1 * | 7/2018 | De Luigi ................. A61K 8/25 |

FOREIGN PATENT DOCUMENTS

EP  0132631 B1  10/1987

OTHER PUBLICATIONS

Make Up For Ever—Let's Gold Palette, Mintel GNPD record ID 6412933, published Mar. 2019, p. 1-4.
M.A.C Art Cosmetics—Supernatural Dazzleshadow, Mintel GNPD record ID 5929345, published Aug. 2018, p. 1-6.
Tou Zhen Cosmetic, Lucenbase Fall in Love Five-Colour Eye Shadow, Mintel GNPD record ID 5762297, published Jun. 2018, p. 1-5.
Parfums Christian Dior, Dior Glow Addict 5 Couleurs Designer All-in-One Professional Eye Palette, Mintel GNPD Yecord ID 5482051, published Mar. 2018, p. 1-9.
Parfums Givenchy, Couture Atelier Palette Mat Eyeshadow 4 Intense Colors, Mintel GNPN record ID 5448207, published Feb. 2018, p. 1-4.
Make-Up Art Cosmetics, M.A.C. Snow Ball Eye Compact, Mintel GNPD record ID 5336239, published Dec. 2017, p. 1-6.
Tarte USA, Rainforest of the Sea Eyeshadow Palette vol. III, Mintel GNPD record ID 5123829, published Oct. 2017, p. 1-5.
Kiko, Neo Muse Eyeshadow Palette, Mintel GNPD record ID 4465275, published Dec. 2016, p. 1-4.
Lise Watier Cosmetiques, Lise Watier Variations de Nude 12-Colour Eyeshadow Palette, Mintel GNPD record ID 3869777, published Mar. 2016, p. 1-2.
Mars Cosmetics, Sarah Moon Duo Eyeshadow, Mintel GNPD record ID 4469881, published Dec. 2016. p. 1-5.

* cited by examiner

*Primary Examiner* — Susan T Tran
(74) *Attorney, Agent, or Firm* — Oblon, McClelland, Maier & Neustadt, L.L.P.

(57) ABSTRACT

Compositions disclosed include pearlescent pigment, talc, boron nitride, and a lipid portion. The lipid portion includes a polydialkylsiloxane, a silicone wax, and a diester of a dicarboxylic acid and a fatty alcohol. The composition is substantially free of water. The composition is generally in the form of a pressed-powder. Methods of use are also disclosed.

16 Claims, No Drawings

ANHYDROUS COSMETIC COMPOSITIONS COMPRISING PEARLESCENT PIGMENT AND A DIESTER

FIELD OF THE INVENTION

The present invention relates to cosmetic compositions comprising pearlescent pigment and a diester and, in particular, such compositions useful for making up the skin.

DISCUSSION OF THE BACKGROUND

Pigmented cosmetic compositions designed to provide optical effects to the skin are known. Such compositions may take various forms, such liquids, creams, loose powders, pressed powders, hot pour compositions, sticks, etc. Pearlescent pigments are often used in such compositions to provide exciting make-up effects. However, these compositions have one or multiple drawbacks in various properties.

The inventors of the instant invention have recognized that many of these prior art compositions that include pearlescent pigments do not simultaneously possess a combination of a properties that would be very advantageous for make-up such as eye-shadows. For example, the present inventors have recognized that it would be desirable to have a composition that provides creamy texture, good color deposition (payoff) and pearlescent intensity, limited flaking, yet also has a pleasant gliding sensation when applied.

Accordingly, certain aspects of the present invention relate to a makeup and/or treatment composition for keratinous materials which can provides one or more of pleasant texture, good color deposition, high pearlescent intensity, limited flaking, and pleasant/convenient application to the skin.

SUMMARY OF THE INVENTION

According to one aspect, the present invention relates to compositions that include at least about 20% by weight of pearlescent pigment, and additionally includes talc and boron nitride. The compositions further include a lipid portion. The lipid portion includes a polydialkylsiloxane, a silicone wax, and a diester. The diester is a diester of a dicarboxylic acid and a fatty alcohol. The concentration by weight of the lipid portion in the composition is less than about 30% by weight. The composition is also substantially free of water. The composition is generally in the form of a pressed-powder.

According to another aspect, the present invention relates to compositions that include at least about 30% by weight of pearlescent pigment, and additionally includes talc and boron nitride. The compositions further include a lipid portion. The lipid portion includes a polydialkylsiloxane, a silicone wax, and diisosteryl malate. The concentration by weight of the lipid portion in the composition is less than about 25% by weight. The composition is also substantially free of water. The composition is generally in the form of a pressed-powder.

According to another aspect, the present invention relates to a method of treating or caring for the skin comprising applying the compositions described above to the skin.

DETAILED DESCRIPTION OF THE INVENTION

As used herein, the expression "at least one" means one or more and thus includes individual components as well as mixtures/combinations.

As used herein, all ranges provided are meant to include every specific range within, and combination of sub ranges between, the given ranges. Furthermore, notably the range description of the type "from 1%, 2% or 5% to about 10%, 15%, or 20% by weight," includes 1%-10%, 1%-15%, 1%-20%, 2%-10%, 2%-15%, 2%-20%, 5%-10%, 5%-15%, and/or 5%-20%. Other than in the operating examples, or where otherwise indicated, all numbers expressing quantities of ingredients and/or reaction conditions are to be understood as being modified in all instances by the term "about," meaning within 10% to 15% of the indicated number.

"Actives basis" as used herein means considering only the particular component of ingredient (e.g., in a composition) and ignoring other chemically unrelated components that may be also be present in the same raw material source of that particular component.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Solids basis" as used herein means considering only components (e.g., in a composition) that are solid at room temperature and ignoring portions of the composition that are liquid, e.g., water and other volatile solvents.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"About," as used herein, when referring to concentrations of various ingredients or components means within 10% or within about 15% of the stated number.

"Anhydrous" means the compositions contain less than about 1% water, such as less than about 0.5% water such as less about 0.1% of water.

All percentages of ingredients herein are listed on an actives basis unless specifically stated otherwise.

The composition of the present invention is generally in the form of a pressed powder, i.e., a composition including powders which have been densified using, for example, mechanical forces.

The compositions of the invention generally include lipids and particulates, and are substantially free of water. The lipids may (co)exist, for example in a fatty phase, such as one having particulates dispersed therein. Many other optional ingredients such as other polymers or various functional ingredients may also be dissolved or dispersed in the fatty phase.

Although the relative proportions of these various components may vary, according to certain embodiments of the invention, the composition includes a concentration of lipids that is less than about 30% by weight of the total composition. In certain embodiments the lipids are present in a concentration by weight of less than about 25% by weight of the total composition.

According to certain other embodiments, the lipids and particulates are present in a weight ratio of lipid to particulate (e.g., inorganic particulate) that is from about 1:6 to about 1:3.

According to certain other embodiments, the composition includes from about 10% by weight to about 30% by weight of lipids and from about from about 60% by weight to about 80% by weight of particulates. According to certain other embodiments, the composition includes from about 10% by weight to about 30% by weight of lipids, from about from about 60% by weight to about 80% by weight of particulates, and from about 2% to 15% of surfactants.

The compositions and methods of the present invention can comprise, consist of, or consist essentially of the essential elements and limitations of the invention described herein, as well as any additional or optional ingredients, components, or limitations described herein or otherwise useful in personal care.

Particulates

As one skilled in the art will readily recognize, "particulate" means any material that remains finely divided in the composition, such as on the order of nanometers to microns. Particulates may be predominantly inorganic (including inorganic particulates having an organic or silicon-based coating, but excluding silicone elastomer particulates). Particulates are meant to encompass, among other materials, boron nitride, talc, perlite, as well as other "filler pigments," "additional pigments," "pearlescent pigments," and "color pigments," described below.

Pearlescent Pigments

Pearlescent pigments are pigments that generally have or approach the luster of natural pearls. Typically, these particulates are plate-like with the broad face of the platelets ranging from about 4 microns to about 1,000 microns across and about 0.5 micron thick. One class of suitable pearlescent pigments include particulates having a mica, synthetic mica, or synthetic fluorphlogopite substrate having one or more coatings formed thereon including: a titanium-containing (e.g., titanium oxide) coating, an iron oxide coating, a tin oxide coating, a chromium oxide coating, and/or an iron blue coating. Another class of suitable pearlescent pigments are those of bismuth oxychloride.

Examples of suitable pearlescent pigments include those available from Eckart (e.g., certain pigments falling under trade names SIMIC, EDELSTEIN, SYNCRYSTAL), BASF (e.g, certain pigments falling under trade names of MEARLITE, PEARL-GLO, CHROMA-LITE, CHIONE), and Merck Performance Materials (e.g, certain pigments falling under trade names of COLORONA).

The concentration of the pearlescent pigment in the composition is at least about 20% by weight, such as at least about 30% by weight and may range from about 20, 30% or 40% to about 40% by weight as from about 50%, 60%, or 70% by weight in the composition.

Boron Nitride

Compositions of the present invention include boron nitride. The inventors have found that boron nitride surprisingly allows the composition to provide a soft gliding sensation and a soft focus for the user. According to certain embodiments the boron nitride has an average particle size from about 5-15 microns.

One notable boron nitride suitable for use in the composition is SOFTOUCH BORON NITRIDE POWDER CC6058, commercially available from Momentive Performance Materials, Waterford, N.Y.

The concentration of the boron nitride in the composition may range from about 1% to about 10% by weight as from about 2% to about 5% by weight in the composition.

Talc

Compositions of the present invention include talc. Talc is a mineral—an inorganic material typically classified as a hydrated magnesium silicate. Talc is soft for a mineral and in compositions of the present invention provides absorption of moisture and oil, softness, and opacity. The talc may be uncoated. In certain embodiments, the talc has a coating at least a portion of which is hydrophobic. According to certain embodiments, the talc has a polydialkylsiloxane (e.g., dimethicone) coating.

One notable talc suitable for use in the composition is LUZENAC 15 M 00v commercially available from Imerys and SA TR 13R from MIYOSHI KASEI the latter having an average particle size of 5-8 μm.

The concentration of the talc in the composition may range from about 2%, 4%, or 6% to about 10%, 12% or 15% by weight in the composition.

Filler Pigments

Compositions of the present invention include one or more filler pigments. The filler pigments provide one or more benefits including opacity/hiding powder to aid in concealing skin imperfections, modification of the texture of the formula, oil absorption, as well as possible mattifying and optical/soft focus effects. Suitable filler pigments include any of various inorganic pigments and the like that provide opacity and may appear white or whitish on the skin and do not otherwise provide strong visible color. Examples of filler pigments include inorganic pigments such as perlite. Other (additional) pigments that may be suitable include for example titanium dioxide, mica, silica, silica silylates, kaolin, as well as bismuth oxychloride, zinc oxide, among others. The filler pigments may be coated or uncoated. In certain notable embodiments the filler pigments in the composition include perlite and/or titanium dioxide. According to certain notable embodiments, the composition is free of silicas such a hydrophobic silica such as silica silylate (particulate hydrophobic silica having surface trialkylsiloxyl groups).

Any of various cosmetic grades of filler pigments are suitable for use in compositions of the present invention. In certain embodiments the filler pigments have an average particle size in a range from about 1 micron to about 100 microns, such as from about 1 micron to about 10 microns.

One notable filler pigment is perlite (e.g., expanded perlite). One notable perlite suitable for use in the composition is OPTIMAT 2550 available from Imerys S.A. The concentration of perlite in the composition may range from about 1%, 2% or 5% to about 10%, 15%, or 20% by weight.

Other notable additional pigments include non-pearlescent pigments, for example, titanium dioxide and various color pigments (other than pearlescent pigments).

Color pigments provide hiding powder to aid in concealing skin imperfections while imparting some additional visible color. Suitable color pigments include any of various inorganic pigments such as iron oxides, ultramarine blue pigments, manganese violet, ferric ferrocyanide and chromium green pigments, and the like. The color pigments may be coated or uncoated. Particularly notable odor pigments (other than pearlescent pigments) include iron oxide.

The concentration of additional pigments such as titanium dioxide and color pigments such as iron oxide in the composition may range from about 0.1%, 0.5%, or 1% to about 2%, 5%, or 10% by weight, including all ranges and subranges therebetween.

Lipids

As described above, compositions of the present invention include a lipid portion. By "lipid" it is meant any of various fatty substances insoluble in water and including, for example, hydrocarbon based fatty substances or silicone-based fatty substances. These may be liquid or solid at room temperature and may be volatile or non-volatile. In certain embodiments, the fatty substances discussed herein are non-volatile.

Examples of suitable fatty substances include oil(s) and/or wax(es). As used herein, by "oils," it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

Suitable examples of compounds of oils include vegetable oils (glyceryl esters of fatty acids, monoglycerides, diglycerides, triglycerides) and fatty esters. Specific non-limiting examples include, without limitation, esters such as isopropyl palmitate, isopropyl myristate, isononyl isonanoate $C_{12}$-$C_{15}$ alkyl benzoates, caprylic/capric triglycerides, ethylhexyl hydroxystearate, silicone oils (such as dimethicone and cyclopentasiloxane), pentaerythritol tetraoctanoate and mineral oil. Other examples of oils include liquid organic ultraviolet filter commonly used for example as UV-absorbing sunscreens such as octocrylene, octyl salicylate, octyl methoxyxcinnamate, among others.

Suitable oils include volatile and/or non-volatile oils. Such oils can be any acceptable oil including but not limited to silicone oils and/or hydrocarbon oils.

According to certain embodiments, the compositions of the present invention may include one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C.

The lipid portion may include waxes. As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C.

The wax may change from the solid to the liquid state reversibly, and/or may have a hardness of more than 0.5 MPa at ambient temperature, and an anisotropic crystalline organization in the solid state.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes (linear, low molecular weight polyethylene waxes), waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

In certain embodiments of the invention, the composition includes both wax and hydrophobic silica. In certain other embodiments the wax and hydrophobic silica are present in a weight ratio of total wax to total hydrophobic silica that is greater than about 4, such as greater than about 4.5, such as from about 4.5 to about 10, such as from about 4.5 to about 6.5. In certain other embodiments, the composition not only has such a total wax to total hydrophobic silica, but also the swellable clay and organic carbonate ester are present in a ratio by weight of swellable clay to organic carbonate ester that is less than about 3.

In certain embodiments of the invention, the composition may include other lipids which may not fall into the definition of wax or oils, such as fatty materials that are semi-solid, pastes or paste-like at room temperature. Suitable examples include shea butter, hydrogenated butters, and any of various partial esters of diglycerin with medium chain fatty acids, such as Bis-Diglyceryl Polyacyladipate-2, commercially available as SOFTISAN 649 from Cremer Oleo of Hamburg, Germany.

Compositions of the present invention include three particular fatty compounds in the lipid portion. The first fatty compound is a polydialkylsiloxane. The polydialkylsiloxane may be a liquid at ambient temperature and pressure such as polydimethylsiloxanes (PDMS) and liquid polyorganosiloxanes comprising at least one aryl group. The polydialkylsiloxanes may be chosen in particular from polydimethylsiloxanes comprising trimethylsilyl end groups, and polydimethylsiloxanes comprising dimethylsilanol end groups, known under the name dimethiconol (CTFA). The polyorganosiloxanes comprising aryl groups are chosen in particular from polydiarylsiloxanes, in particular polydiphenylsiloxanes, and polyalkylarylsiloxanes.

In certain embodiments the polydialkylsiloxane is in the form of a liquid silicone that is added to and blended with other components of the composition. In another embodiment, the polydialkylsiloxane exists as a coating on one or more of the particulates in the composition. In one notable embodiment, the polydialkylsiloxane exists as a coating on the talc, such as described in the "TALC" section, above. The polydialkylsiloxane may be present in the composition in concentration by weight from about 0.05%, 0.1%, 0.25. or 0.5% to about 0.5%, 1%, 2% or 10%.

The second fatty compound is a silicone wax. Silicone waxes are generally wax materials that include dialkylsiloxane groups. The silicone wax, in certain embodiments includes a plurality of siloxane repeat units and at least one C8-C40 alkyl chain bonded thereto. Examples of silicone waxes include cetyl dimethicone, stearyl dimethicone, caprylyl dimethicone and the like. Cetyl dimethicone is particularly notable.

The silicone wax may be present in the composition in concentration by weight from about 2%, 5%, or 10% to about 15%, 25%, or 30%.

The third fatty compound is a diester of a dicarboxylic acid and a dicarboxylic acid. In one notable embodiment, the diester of a dicarboxylic acid and a dicarboxylic acid is diisosteryl malate, such as SCHERCEMOL DISM ESTER or Diisostearyl Dimer Dilinoleate, both available from Lubrizol Advanced Materials, Diisosteryl malate is particularly notable.

The diester of a dicarboxylic acid and a dicarboxylic acid may be present in the composition in concentration by weight from about 0.5%, 1%, or 5% to about 10%, 20%, or 30%.

The concentration of lipids (total) in the composition may be from about 5%, 10% or 15% by weight to about 15%, 20% or 30% by weight, including all combinations of such ranges, relative to the total weight of the composition.

Surfactants

Compositions of the present invention include one or more surfactants or emulsifiers. Surfactants and emulsifiers modify surface tension and can provide enhanced skinfeel and/or product stability. Surfactants generally include a hydrophilic portion and a hydrophobic portion. According to certain embodiments of the invention the surfactant is non-ionic. Particularly notable surfactants include magnesium stearate, polysorbates, sucrose esters of fatty acids, and PEG-modified tatty alcohols, and the like. Magnesium stearate and sucrose esters of fatty acids are particularly notable. The surfactant/emulsifier may be present in the composition in concentration by weight from about 1%, 2%, 5%, or 10% to about 12%, 15%, or 20%.

Other Ingredients

Compositions of the present invention may optionally include other functional ingredients such as those that can be readily dissolved, dispersed or suspended in the composition. These may include other particulate materials (organic, silicone-based); polymers such as for thickening/rheology modifying; preservatives; dyes, fragrances; solvents including alcohols or glycols; antioxidants; sunscreens; vitamins; and the like. A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

The other ingredients may be present in the composition in concentrations up to about 20%, such as from about 0%, 2%, or 5% to about 10%, 15%, or 20%, including all ranges and subranges therebetween.

According to preferred embodiments of the present invention, methods of treating, caring for and/or making up a keratinous material by applying compositions of the present invention to the keratinous material in an amount sufficient to treat, care for and/or make up the keratinous material are provided. According to yet other preferred embodiments, methods of enhancing the appearance of a keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratinous material in an amount sufficient to treat, care for and/or make up the keratinous material, to cover or hide defects associated with keratinous material, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Compositions and Testing

Five compositions were prepared. The first, Inventive Example Ex 1, with concentrations by weight of ingredients shown in Table 1, was made by combining boron nitride, dimethicone-coated talc, and additional pigments and mixing at high speed for two-three minutes. Pearlescent pigments were then added and mixed on low speed for 30 seconds. Diisostearyl malate, cosmetic oil, preservative, and emulsifier were then added and mixed on low speed for one minute. The mixture was sifted through an 850 micron sieve and pressed using a hydraulic manual press at 1200 psi (held for 3 seconds) and pressed, 3.3 grams into a rectangular pan.

TABLE 1

|  | Ex 1 | Comp 1 | Comp 2 | Comp 3 | Comp 4 |
| --- | --- | --- | --- | --- | --- |
| Boron Nitride | 3 | 0 | 3 | 3 | 3 |
| Dimethicone-coated talc | 5 | 5 | 0 | 5 | 5 |
| Pearlescent Pigments and Other Pigments | 67.5 | 70.5 | 72.5 | 67.5 | 67.5 |
| Diisostearyl malate | 12 | 12 | 12 | 12 | 0 |
| Silicone Wax | 4 | 4 | 4 | 0 | 4 |

TABLE 1-continued

|  | Ex 1 | Comp 1 | Comp 2 | Comp 3 | Comp 4 |
|---|---|---|---|---|---|
| Cosmetic Oils | 4 | 4 | 4 | 8 | 16 |
| Surfactants | 4 | 4 | 4 | 4 | 4 |
| Other Ingredients | 0.5 | 0.5 | 0.5 | 0.5 | 0.5 |

Comparative examples were made by replacing various ingredients in Inventive Example Ex 1. Specifically, for Comparative Example Comp 1 boron nitride was removed and replaced (QS) with uncoated talc; for Comparative Example Comp 2 Talc/Dimethicone was removed and replaced with uncoated talc; for Comparative Example Comp 3 silicone wax was removed and replaced with Synthetic Wax; for Comparative Example Comp 4 Diisostearyl Malate was removed and replaced with Caprylic/Capric Triglyceride.

The pressed eyeshadow samples were evaluated by 5 different evaluators who have experience in evaluating eyeshadow formulas and are able to differentiate and properly quantify the following eyeshadow attributes: sensory feel (creamy, dry), flaking, glazing, pick up/pay off, pearlescence intensity of swatch, pearl laydown in pan. The expertise of the evaluators stems from their extensive working background in powder formulation. The evaluations were using finger as the applicator and skin on the arm as the substrate. Visual and sensory evaluation was employed to determine the eyeshadow attributes during the application of powder on the arm and to evaluate the finished look after the application was completed The pressed eyeshadow samples of modified formulas were evaluated and compared to Inventive Example Ex 1. The following are the attributes were looked at: sensory feel (creamy, dry), flaking, glazing, pick up/pay off, pearlescence intensity of swatch, pearl laydown in pan. The results are shown in Table 2, below:

TABLE 2

| Ref. | Modif. | Sensory | Pick Up/ Payoff | Glazing | Degree of Pearlescence | Pearl Laydown | Flakiness |
|---|---|---|---|---|---|---|---|
| Ex. 1 | — | creamy | good | no | intense | vibrant | no |
| Comp. 1 | Remove boron nitride | dry | good | yes | intense | vibrant | yes |
| Comp. 2 | Remove talc/ dimethicone | dry | good | no | intense | vibrant | yes |
| Comp. 3 | Remove cetyl dimethicone (silicone wax) | dry | poor | no | Poor, flat | Poor | no |
| Comp. 4 | Remove diisostearyl malate | dry | poor | no | Poor, flat | Poor | no |

The results show that for a formula with at least about 20% by weight of pearlescent pigment; boron nitride, talc, boron nitride polydialkylsiloxane, silicone wax, and a diester of a dicarboxylic acid and a fatty alcohol are surprisingly needed to achieve a balance of sensory attributes, pick up/payoff, reduced glazing, pearlescent intensity, pearl laydown, and reduced flakiness.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. accordingly, the description is not intended to limit the invention to the form disclosed herein. Also, it is intended to the appended claims to construed to include alternative embodiments.

What is claimed is:

1. A composition in the form of a pressed powder, comprising:
    at least about 30% by weight of pearlescent pigment;
    talc;
    boron nitride; and
    a lipid portion comprising a polydialkylsiloxane, a silicone wax, and diisosteryl malate in a concentration by weight from about 5% to about 20%;
    wherein the concentration by weight of the lipid portion is less than about 25%; and
    wherein the composition is substantially free of water.

2. The composition of claim 1 wherein the pearlescent pigment is present in a concentration by weight from about 30% to about 70%.

3. The composition of claim 1 wherein the silicone wax is present in a concentration by weight from about 10% to about 30%.

4. The composition of claim 1 wherein the silicone wax comprises a plurality of siloxane repeat units and at least one C8-C40 alkyl chain bonded thereto.

5. The composition of claim 1 wherein the boron nitride is present in a concentration by weight from about 1% to about 10%.

6. The composition of claim 1, further comprising perlite.

7. The composition of claim 6 wherein the perlite is present in a concentration by weight from about 1% to about 20%.

8. The composition of claim 1, further comprising one or more surfactants.

9. The composition of claim 1 wherein magnesium stearate is present in a concentration by weight from about 2% to about 15%.

10. The composition of claim 1, wherein the talc is present in a concentration by weight from about 2% to about 12%.

11. The composition of claim 10 wherein the talc is coated with dimethicone.

12. The composition of claim 1, wherein the pearlescent pigment is present in a concentration by weight from about 40% to about 70%, wherein silicone wax is present in a concentration by weight from about 10% to about 30%, and wherein the talc is present in a concentration from about 2% to about 12%, and wherein the boron nitride is present in a concentration by weight from about 2% to about 5%.

13. A method of making up skin comprising applying the composition of claim 1 thereto.

14. The composition of claim 1 wherein the composition does not contain microcrystalline wax.

15. The composition of claim 1, further comprising one or more surfactants.

16. The composition of claim 15 wherein the one or more surfactants comprise magnesium stearate.

* * * * *